(12) United States Patent
Conner et al.

(10) Patent No.: US 7,815,123 B2
(45) Date of Patent: Oct. 19, 2010

(54) STERILE MEDICATION IDENTIFICATION DELIVERY AND APPLICATION SYSTEM

(75) Inventors: Nora M. Conner, Elyria, OH (US);
Megan T. Schumacher, Avon Lake, OH (US)

(73) Assignee: ORventions LLC, Westlake, OH (US)

( * ) Notice: Subject to any disclaimer, the term of this patent is extended or adjusted under 35 U.S.C. 154(b) by 411 days.

(21) Appl. No.: 11/936,386

(22) Filed: Nov. 7, 2007

(65) Prior Publication Data

US 2009/0114729 A1    May 7, 2009

(51) Int. Cl.
| | |
|---|---|
| *G06F 17/00* | (2006.01) |
| *G06F 19/00* | (2006.01) |
| *G06Q 30/00* | (2006.01) |
| *G06Q 90/00* | (2006.01) |
| *G06K 19/00* | (2006.01) |
| *G06K 19/06* | (2006.01) |
| *B65B 61/00* | (2006.01) |
| *B65B 51/08* | (2006.01) |
| *B65B 55/04* | (2006.01) |
| *B67B 1/03* | (2006.01) |
| *G09F 3/10* | (2006.01) |

(52) U.S. Cl. ................ 235/487; 235/375; 235/385; 235/492; 235/493; 53/415; 53/426; 40/638

(58) Field of Classification Search ............ 40/630, 40/638, 310; 206/534, 459.5, 438, 363, 64, 206/370, 570, 572, 604, 459.1, 210; 235/375, 235/487, 492, 493, 385; 29/428; 53/425, 53/426
See application file for complete search history.

(56) References Cited

U.S. PATENT DOCUMENTS

| | | | | |
|---|---|---|---|---|
| 3,460,742 | A * | 8/1969 | Langdon | ............ 206/439 |
| 3,616,898 | A * | 11/1971 | Massie | ............ 206/216 |
| 3,724,651 | A * | 4/1973 | Link | ............ 206/363 |
| 3,885,562 | A | 5/1975 | Lampkin | |
| 3,926,311 | A * | 12/1975 | Laske | ............ 206/439 |
| 3,967,729 | A | 7/1976 | Tanner, II | |
| 4,022,324 | A * | 5/1977 | Schuster | ............ 206/439 |
| 4,197,947 | A * | 4/1980 | Zaidi | ............ 206/438 |
| 4,449,631 | A * | 5/1984 | Levenberg et al. | ....... 206/459.1 |

(Continued)

OTHER PUBLICATIONS

Cardinal Health: Presource® Medication Labels and Markers, www.cardinal.com, Mar. 23, 2010.

(Continued)

*Primary Examiner*—Daniel Walsh
(74) *Attorney, Agent, or Firm*—Fay Sharpe LLP (57) ABSTRACT

This disclosure is directed towards a method and apparatus provided for improved sterile labeling on medications, solutions and medical supplies. The apparatus includes a sterile label, including associated corresponding medical product information. The sterile label is contained inside a sterile cavity housing which is formed from a first and second sheet of flexible plastic or other material. The flexible plastic material is bound together along its peripheral edges by an adhesive or heat sealing process. In this form, the flexible plastic or other material creates a package which may be peeled apart, enabling the label to be delivered or flipped to a sterile field while maintaining sterility. The label may contain on it many types of information corresponding to a medication. Furthermore, information can be added by a user. The disclosure makes the medication labeling system more accurate, safe and legible.

19 Claims, 8 Drawing Sheets

U.S. PATENT DOCUMENTS

| | | | | |
|---|---|---|---|---|
| 4,921,277 | A * | 5/1990 | McDonough | 283/81 |
| 4,947,620 | A * | 8/1990 | Carter | 53/425 |
| 4,947,867 | A * | 8/1990 | Keeton | 128/846 |
| 4,951,815 | A * | 8/1990 | Ulbrich | 206/213 |
| 5,033,252 | A * | 7/1991 | Carter | 53/425 |
| 5,052,558 | A | 10/1991 | Carter | |
| 5,117,981 | A * | 6/1992 | Crawford et al. | 206/570 |
| 5,186,499 | A * | 2/1993 | Mason | 283/81 |
| 5,279,058 | A * | 1/1994 | Kohn | 40/638 |
| 5,325,987 | A * | 7/1994 | Alpern et al. | 229/122.34 |
| 5,356,006 | A * | 10/1994 | Alpern et al. | 206/363 |
| 5,585,899 | A | 12/1996 | Palumbo et al. | |
| 5,692,640 | A | 12/1997 | Caulfield et al. | |
| 5,725,169 | A * | 3/1998 | Odagiri | 242/344 |
| 6,033,392 | A * | 3/2000 | Frey et al. | 604/403 |
| 6,085,907 | A * | 7/2000 | Hochmeister et al. | 206/569 |
| 6,228,324 | B1 * | 5/2001 | Hasegawa et al. | 422/30 |
| 6,428,867 | B1 * | 8/2002 | Scott et al. | 428/40.1 |
| 6,485,979 | B1 * | 11/2002 | Kippenhan et al. | 436/1 |
| 6,589,622 | B1 * | 7/2003 | Scott | 428/40.1 |
| 6,685,227 | B2 | 2/2004 | Merry et al. | |
| 6,929,837 | B2 * | 8/2005 | Morrison | 428/40.1 |
| 6,955,002 | B2 * | 10/2005 | Sandel et al. | 40/638 |
| 6,994,249 | B2 | 2/2006 | Peterka et al. | |
| 7,299,981 | B2 * | 11/2007 | Hickle et al. | 235/385 |
| 7,331,463 | B2 * | 2/2008 | Hickey | 206/570 |
| 7,381,288 | B2 * | 6/2008 | Aparicio et al. | 156/277 |
| 2002/0026043 | A1 * | 2/2002 | Edmonds | 536/23.5 |
| 2003/0165653 | A1 * | 9/2003 | Morrison | 428/42.3 |
| 2004/0056478 | A1 * | 3/2004 | Bruce | 283/81 |
| 2005/0218032 | A1 * | 10/2005 | Maddock et al. | 206/581 |
| 2005/0268505 | A1 | 12/2005 | Sandel et al. | |
| 2006/0058804 | A1 * | 3/2006 | Mollstam | 606/80 |
| 2006/0096877 | A1 * | 5/2006 | Khajavi et al. | 206/363 |
| 2006/0100541 | A1 * | 5/2006 | Aparicio et al. | 600/562 |
| 2006/0266368 | A1 | 11/2006 | Heintz | |
| 2007/0187475 | A1 | 8/2007 | MacLeod | |
| 2007/0199848 | A1 | 8/2007 | Ellswood et al. | |
| 2007/0254128 | A1 | 11/2007 | Lober | |
| 2007/0295635 | A1 * | 12/2007 | Rivero | 206/538 |
| 2008/0035659 | A1 | 2/2008 | Ricker et al. | |
| 2008/0116106 | A1 * | 5/2008 | Lampropoulos et al. | 206/570 |
| 2008/0174102 | A1 * | 7/2008 | McKinnon et al. | 283/70 |
| 2008/0220227 | A1 * | 9/2008 | Keeney et al. | 428/203 |
| 2008/0283426 | A1 * | 11/2008 | Primer et al. | 206/232 |
| 2008/0303265 | A1 | 12/2008 | Kaufman | |
| 2009/0114729 | A1 * | 5/2009 | Conner et al. | 235/494 |
| 2009/0236259 | A1 * | 9/2009 | Hicks | 206/571 |
| 2009/0266728 | A1 * | 10/2009 | Turner et al. | 206/363 |
| 2009/0266889 | A1 * | 10/2009 | Turner et al. | 235/385 |
| 2010/0088116 | A1 * | 4/2010 | Eisenberg et al. | 705/3 |

OTHER PUBLICATIONS

Centurion® Label Systems, www.tshsc.com, Mar. 23, 2010.
Dasco Systems, www.dascosystems.com, Mar. 23, 2010.
Health Care Logistics, www.healthcarelogistics.com, Mar. 23, 2010.
Medi-Dose, Inc., EPS® Stock Sterile Labels, www.medidose.com, Mar. 23, 2010.
Medline Industries, Inc., www.medline.com, Mar. 23, 2010.
Merit Medical Systems, Inc., PAL, Pen and Label™, www.merit.com, Mar. 23, 2010.
Sandel Medical Industries LLC, Correct Medication Labeling System™, www.sandelmedical.com, Mar. 23, 2010.
The St. John Companies, Inc., www.stjohninc.com, Mar. 23, 2010.
TimeMed Labeling Systems, Inc., www.timemed.com, Mar. 23, 2010.
Viscot Medical LLC, www.viscot.com, Mar. 23, 2010.
Xodus Medical, www.xodusmedical.com, Mar. 23, 2010.

* cited by examiner

STERILE MEDICATION IDENTIFICATION DELIVERY AND APPLICATION SYSTEM

BACKGROUND OF THE DISCLOSURE

This disclosure relates to an apparatus and method for medical products labeling. More particularly, this disclosure relates to sterile labeling and packaging of medications, solutions, supplies and other medical material that may be used in a sterile environment, such as an operating room.

While the disclosure is particularly directed towards a peel pack containing one or more sterile labels, which may be applied to medications for use within a sterile field, and thus will be described with specific reference thereto, it will be appreciated that this disclosure may have usefulness in other fields and applications. For example, this disclosure may be used in a variety of settings where sterility is useful and/or mandated.

By way of background, medical errors are responsible for many injuries and deaths in the world. Many of these medical errors are medication errors. Medication errors are preventable episodes that cause or lead to inappropriate medication administration and cause a patient harm while the medication is under the control of the health care professional, patient and/or consumer. Studies show that when medication errors occur in the operating room, they are more likely to cause the patient harm than when they occur in other areas in the hospital and/or in the patient's home. In an operating room environment, many of these medication errors are the result of unlabeled medications and solutions used within the sterile field.

Generally, medications, solutions and supplies are delivered to hospitals in containers supplied by the manufacturers. The materials inside of these containers are sterile. However, the outside of the containers are not sterile. This is in part because the outside of the containers are handled outside of the sterile field. In the operating room, a circulating nurse may carry the container, open it and dispense the sterile contents into a container within the sterile field without contamination of the sterile field. The circulating nurse often works with a scrub nurse who is dressed in a sterile gown and gloves and maintaining a sterile field. The scrub nurse handles the sterile medication without compromising the sterility. The circulating nurse initiates the process of dispensing the medication to the sterile field. The circulating nurse/licensed medical professional handles the unsterile container (the contents of which are sterile) and pours the medication, using aseptic technique, onto the sterile field. The scrub nurse must then label the container and any additional apparatus used to administer the medication from that point. The medications are labeled according to practice standards mandated by various government agencies such as Centers for Medicare and Medicaid Services (CMS); and, other accrediting organizations such as the American Nurses Association (ANA), Joint Commission on Accreditation of Health Organizations (JCAHO), etc. Current specific requirements include medication/solution name, strength, amount (if not apparent), diluent (if applicable) and expiration date/time.

These standards are in place to help reduce medication errors. Therefore, the scrub nurse must apply a sterile label to the container for these medications, at the time the medications are delivered to the sterile field. For example, if a medication is dispensed into a cup, basin (or receptacle) and then subsequently drawn into a syringe, the cup or basin and the syringe must both be labeled with the name of the medication and other pertinent information using a sterile label.

This process of writing out all pertinent information on a label can be time consuming and dangerous for a scrub nurse who may have other urgent duties. However, a circulating nurse generally is not able to handle the labeling procedures because the circulating nurse is not within the sterile field and would contaminate the sterile field if he or she labels the medication.

Therefore, there is a need in the industry to provide a system and apparatus which will reduce the amount of labeling errors in the operating room. Furthermore, there is a need in the industry to allow for flexibility of labeling medication, supplies, and other materials without compromising sterility. There is also a need in the industry to make the labeling process more efficient and less susceptible to human error.

The present disclosure contemplates a new and improved method that resolves the above-referenced difficulty and others.

SUMMARY OF THE DISCLOSURE

A method and system for delivering sterile labels to a sterile field by a circulating medical professional is provided. This disclosure allows for a peel pack that contains one or more sterile labels that contain information directly corresponding to a particular medication or solution, removably attached to the container of such medication or solution—regardless of the characteristics of the original package i.e. vial, bottle, or flat-type container. The corresponding sterile labels, enclosed in a transparent peel pack, are then attached to the original container and in certain cases secured with a tamper resistant transparent attachment. A peel pack is used to enclose an item where the item may be dispensed without being touched by the user. Through this disclosure a licensed medical professional can detach the peel pack from the primary container, open the peel pack, and dispense sterile labels to a scrub nurse in the sterile field without compromising the sterility of the label. Through this disclosure, the scrub nurse can then immediately and accurately verify the label, dispense and prepare the medication according to recommended practices. The scrubbed medical professional may also write down the date and time of dispensing or other pertinent information on the labels.

In one aspect of the disclosure, an apparatus for sterile labeling on medications, solutions and medical supplies comprises, a sterile label including associated corresponding medical products information and a first and second sheet of flexible plastic, metal, foil or other suitable sheet material, each sheet having peripheral edges, where at least two of the peripheral edges on each of the sheets forms a joint bonded by the adhesive or through heat sealing. The first and second sheets form an internal cavity that may house at least one label, and the entire package containing the label(s) may be sterilized after insertion of the label; and, where the sterilized label(s) may be applied to a container within a sterile field while maintaining sterility.

According to another aspect of the present disclosure, the first and second sheets are transparent.

According to another aspect of the present disclosure, the sterile labels are water proof and constructed out of synthetic stock.

According to another aspect of the present disclosure, the corresponding medical products information includes manufacturing information, medication name, concentration, diluents, dosage, expiration information, route of administration, lot number and areas for inclusion of amount and time the medication is dispensed to the sterile field.

According to another aspect of the present disclosure, the apparatus includes a set of sterile labels suitable for labeling a plurality of associated medical accessories.

In accordance with another aspect of the present disclosure, the apparatus includes that the sterile labels have bar codes specific to the corresponding medical product, and space for additional information that may be added by a user.

In accordance with yet another aspect of the present disclosure, a method for delivering sterile labels to a sterile field by a licensed medical professional comprised of peeling apart a package containing at least one sterile label having specific information about a corresponding medication where the package includes a first and second sheet of flexible plastic material or other flexible material bound together by an adhesive or heat sealing on the sheet's peripheral edges where the sheets together form a cavity that can be sterilized and maintain its sterility until opened, and have the ability to deliver the sterile label from the package into a sterile field, while maintaining sterility.

In accordance with another aspect of the present disclosure, the method includes flipping the sterile label onto a sterile surface.

According to another aspect of the present disclosure, the method includes placing the sterile label onto a sterile apparatus.

According to yet another aspect of the present disclosure, a method of manufacturing a sterile labeling system comprises printing a label having medical information corresponding to a medical product, enclosing the label inside of at least two sheets of flexible material that are bound together with an adhesive or heat sealed, where the sheets of material together form a pocket in which the label is held. The package of labels is then sterilized and attached to its corresponding original container or packaging containing the original sterile medical product.

Another aspect of the present disclosure includes printing the information on the labels with indelible ink or indelible phosphorescent ink.

Another aspect of the disclosure is that the package of sterile labels may in some cases be attached to the original container and secured with a tamperproof attachment.

Another aspect of the disclosure would provide inclusion of an indicator strip or dot to disclose whether the package of labels has been subjected to a sterilization process.

DESCRIPTION OF THE DRAWINGS

The presently described embodiments exist in the construction, arrangement and combination of the various parts of the device and steps of the method whereby the objects contemplated are attained as hereinafter more fully set forth specifically pointed out in the claims and illustrated in the accompanying drawings in which:

DETAILED DESCRIPTION

Figure 1:
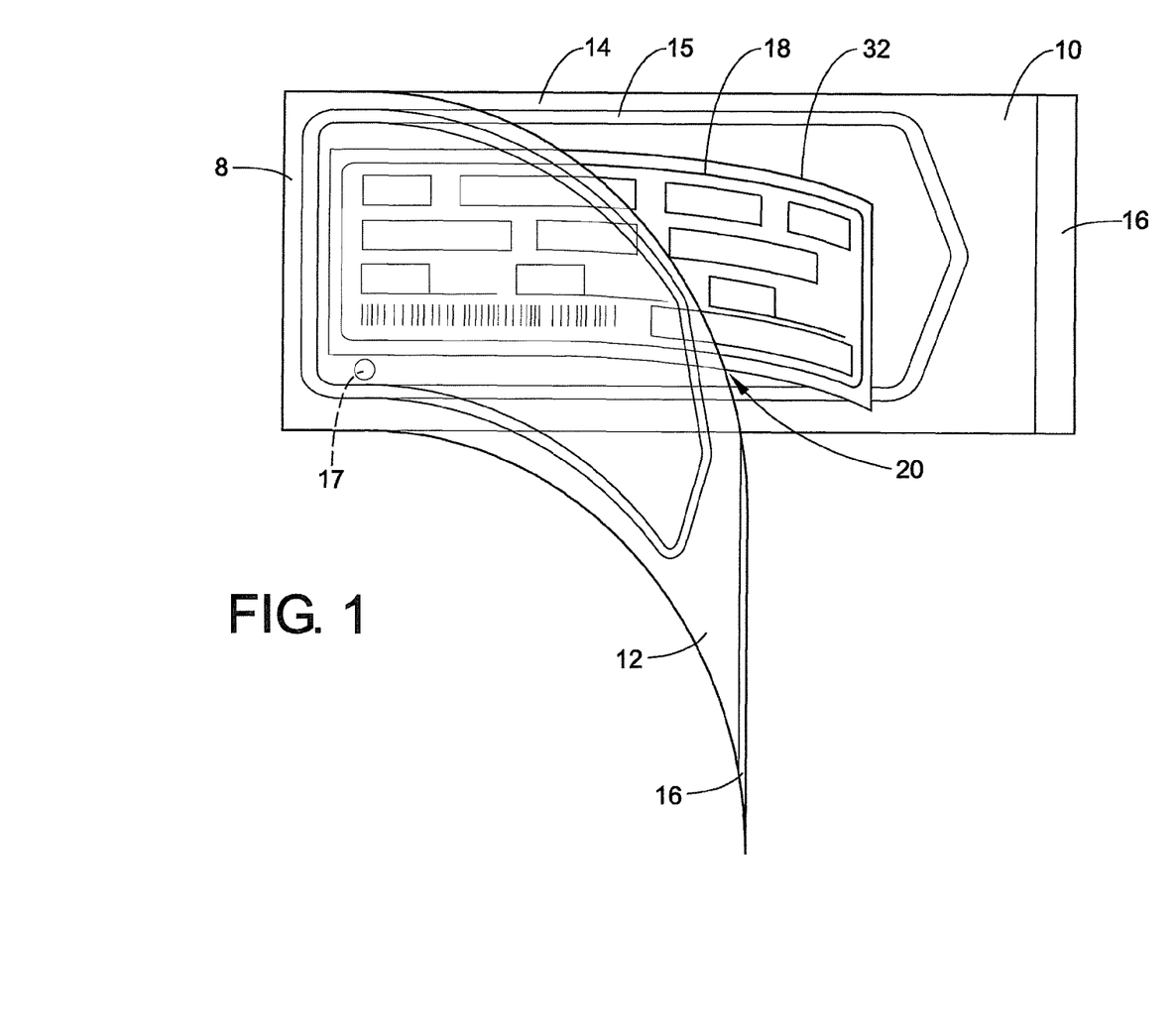
FIG. 1 illustrates one embodiment of the sterile labeling apparatus according to the present disclosure.

Referring now to the drawings wherein the showings are for purposes of illustrating the disclosed embodiments only and not for purposes of limiting the same. FIG. 1 shows one embodiment of the sterile labeling system. The system includes two sheets of flexible plastic material having peripheral edges. The edges are bonded together with an adhesive to allow creation of a sterile pocket or cavity in which one or more sterile labels are housed. The bound sheets form a peel pack 8. The sterile label includes various elements from the corresponding medication, solution, or supply label. In operation, the first and second sheets of plastic material can be peeled back from one another creating an opening from which the sterile label may be dispensed. The sterile label then can be placed upon a sterile container which may house the medication or solution. This method can be performed by a licensed medical professional in the circulating and scrub roles. Using this system, the licensed medical professional in the circulating role, may place the sterile label onto the sterile field, using aseptic technique, without compromising the sterility of the label.

It should be noted that FIG. 1 displays but one embodiment of this disclosure. It should be appreciated that other embodiments exist and still fall within the scope of the claims.

Still referring to FIG. 1 which shows an embodiment of the labeling system. The labeling system includes a first and second sheet of flexible plastic material 10, 12. Each sheet has peripheral edges. In this embodiment the first and second sheet are similar sizes, however, this need not be the case. The first and second sheet 10, 12 may encompass a variety of different shapes and sizes.

The first and second sheet 10, 12 include peripheral edges 14, which may be in communication with one another. In this form the peripheral edges 14 of each sheet are joined together by a band of adhesive, or a heat seal, to form a joint 15. It should be noted that the joint 15 at peripheral edges 14 need not be at the extreme far edges of the sheet. The joint 15 and peripheral edges serve the purpose of forming an isolated internal cavity 20 between the two sheets 10, 12. Whereas, the internal cavity 20 is generally completely enclosed for sterility to be maintained after the package is subjected to a sterilization process. The two sheets may also have separation flaps 16 between the two of them. Generally, these separation flaps 16 are not joined with the adhesive.

The first and second sheet 10, 12 may also be transparent. In this form, the label may show through the sheets 10, 12 so that the user will know which label 18 is inside without opening the peel pack. This may also aid in reducing human errors resulting from application of the wrong label to an accessory medical container.

The first and second sheet of flexible plastic material 10, 12 contain within the cavity 20 at least one sterile label 18. After sterilization, the cavity 20 remains sterile as a result of the fact that it does not come in contact with any non-sterile environment outside of the first and second sheet 10, 12. The outside of the first and second sheet 10, 12 may be handled by a non-sterile licensed medical professional, whereas the label 18 on the inside will remain sterile to be handled within the sterile field.

The peel pack may also include a sterilization indicator 17. The sterilization indicator may be placed in the cavity 20, or on the face of the outer flexible sheets 10, 12. In this form, the sterilizing indicator can be seen through the clear sheets, 10, 12 without opening the pack. The sterilization indicator is generally used to indicate that an item has been subjected to a sterilization process. In some embodiments it appears as stripe, however, it may appear as a dot or other object.

The label 18 may contain various elements from the original product label. In one embodiment, the label contains manufacture information. In another embodiment the label 18 has a bar code specific to a corresponding medical product. In another embodiment the label 18 includes space for additional variable information to be added. This additional information may include the time and date in which the original packaging for the corresponding medication was opened. The label 18 may also include expiration information, the name of the medication(s), solutions and/or supplies, dosage, concentration, etc.

The label 18 may also be constructed out of synthetic stock. It may also be useful for the label to be waterproof. The label 18 may also contain its own adhesive to aid a medical professional in applying the label to another medical accessory such as a syringe, a basin, a cup, a tub, etc. The sterile label 18 may also be part of a set in which many labels can be applied through a plurality of associated medical accessories. The sterile label 18 may be produced at the time of manufacturing its corresponding medication. In this sense the sterile label 18 will contain all of the information that is pertinent according to the requirements and/or manufacturer's specification and specifically matched to the original medication container. Furthermore, this information may be printed with phosphorescent ink that may be visible in the dark. The package containing the label may also, in some embodiments, be secured with a tamper resistant attachment. (See FIG. 3) This may assist in securing the label from being removed at the inappropriate time.

Figure 2:
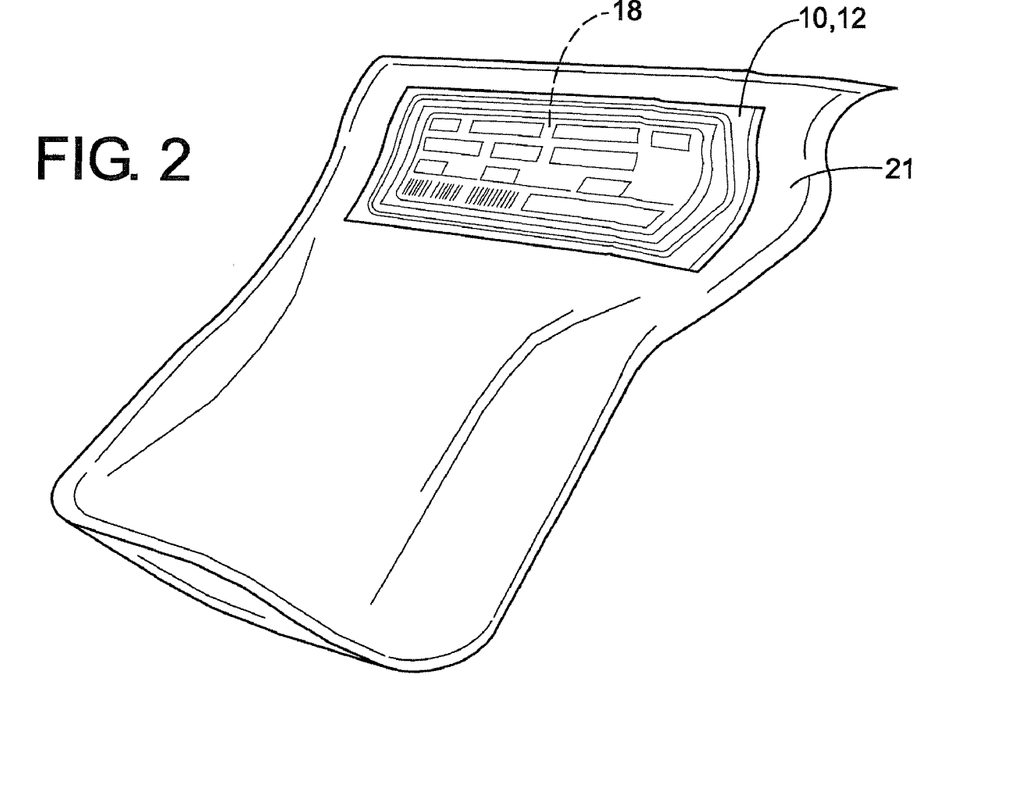
FIG. 2 illustrates another embodiment of the sterile labeling apparatus as applied according to the present disclosure.
Figure 3:
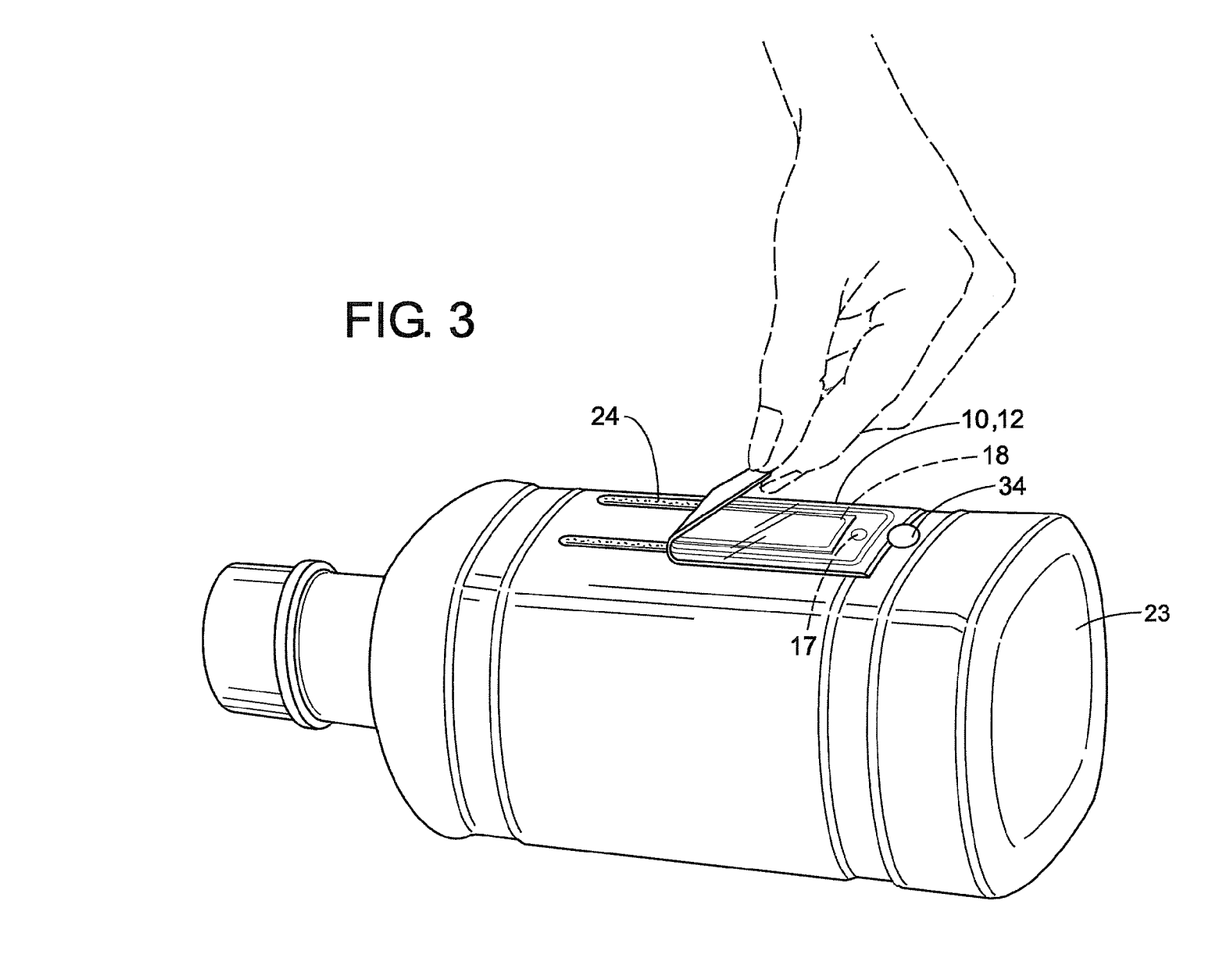
FIG. 3 illustrates an embodiment of the labeling apparatus as applied according to one of the steps of the method.

FIGS. 2 and 3 show that the peel pack may be applied to a variety of surfaces and package types. FIG. 2 shows that the sterile label 18 within the peel pack may be attached to a flat type package 21. FIG. 3 illustrates an embodiment of the apparatus according to one of the steps of the disclosure. FIG. 3 shows the peel pack containing the label 18 being peeled from a large bottle 23. This is but another embodiment of the disclosure demonstrating how the apparatus containing the label 18 may be manufactured in a variety of sizes and shapes. The label 18 and apparatus may be custom designed to fit a particular need depending on the medication and use. The adhesive 24 also allows the apparatus containing the label 18 to be affixed to a wide variety of surfaces and container types such as flat packs, bottles containing sterile medication or solutions, or other containers, medicines, surgical supplies and the like.

The peel pack also includes a tamper resistant attachment 34. Tamper resistant attachment features are commercially available. They are used extensively on over the counter drug packages and on other consumer and professional packaging. This attachment 34 is shown as a dot, but may come in many forms like a strip or a band. The attachment may assist in showing that the apparatus has not been detached from the original medication container. The attachment 34 may be on the outside of the pack as shown here. When the peel pack is removed from the original medication container, the tamper resistant attachment may change color or other outward appearance, to alert the user to such a condition. The apparatus may also include a sterilization indicator 17. This indicator is shown as a dot, but may come in many forms, such as a strip or band. The sterilization indicator may assist in showing the apparatus has been subjected to a sterilization process by changing color or other observable characteristics.

Figure 4:
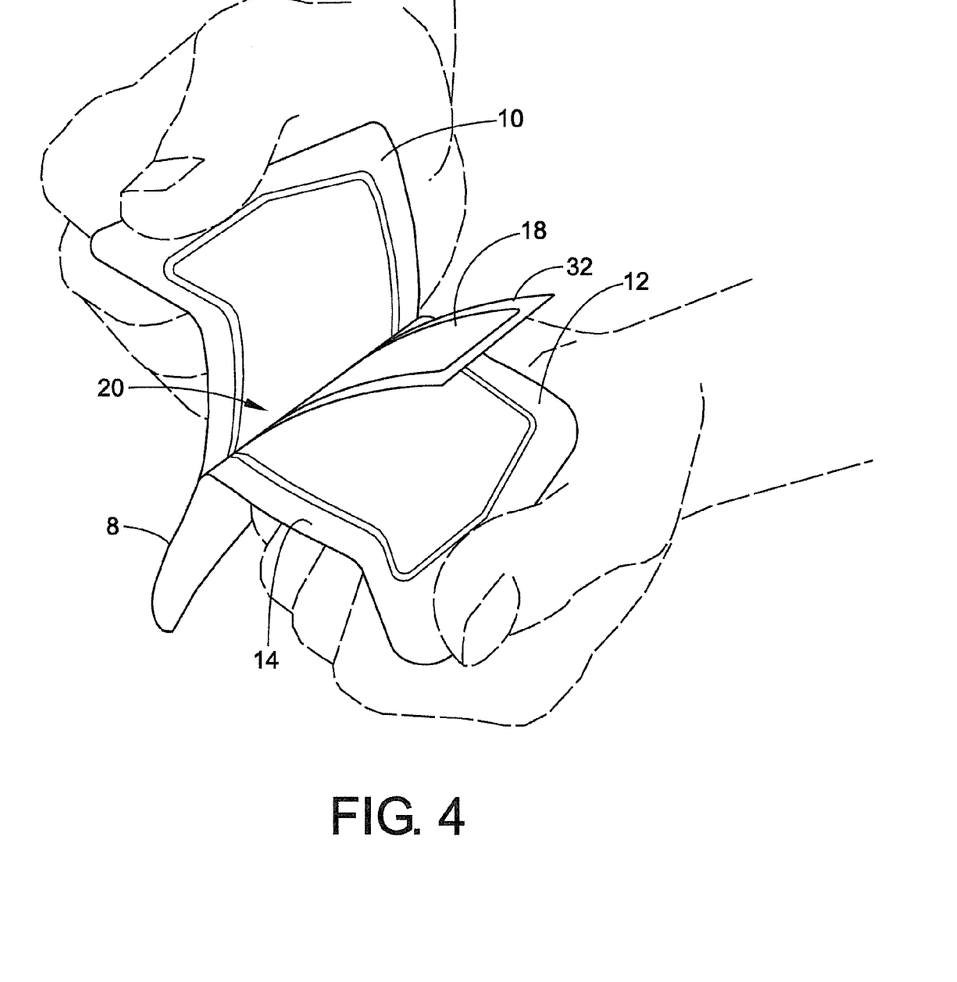
FIG. 4 illustrates an embodiment of the labeling system as applied according to one of the steps of the method.

Now referring to FIG. 4, which illustrates one of the steps of the method according to the present disclosure. FIG. 4 illustrates a user peeling apart the first and second sheets of flexible plastic material 10, 12 which are bound together by an adhesive or heat sealing on at least one of the each sheet's peripheral edges 14. These peripheral edges bound together form a cavity 20 that may be sterilized by a sterilization process applied before or after the cavity is enclosed. This step normally occurs after a circulating nurse has removed the peel pack 8 from the container for the medicine of supply to which it pertains.

As shown in FIG. 4, the user may pull apart the package without touching the sterile label 18. This will aid in maintaining the sterility of the label 18 so that it may be delivered to a sterile field. The action allows for the user to only come in contact with the outside of the first and second sheet 10, 12. The outside of these sheets generally are not sterile because of their exposure to a non-sterile field. They do however, protect the cavity portion on the inside of the first and second sheet 10, 12 from becoming contaminated. In turn, the label 18 contained therein also remains sterile and is not contaminated. If the label comes in contact with a non-sterile surface, the label may be flash sterilized to return it to a sterile state.

Figure 5:
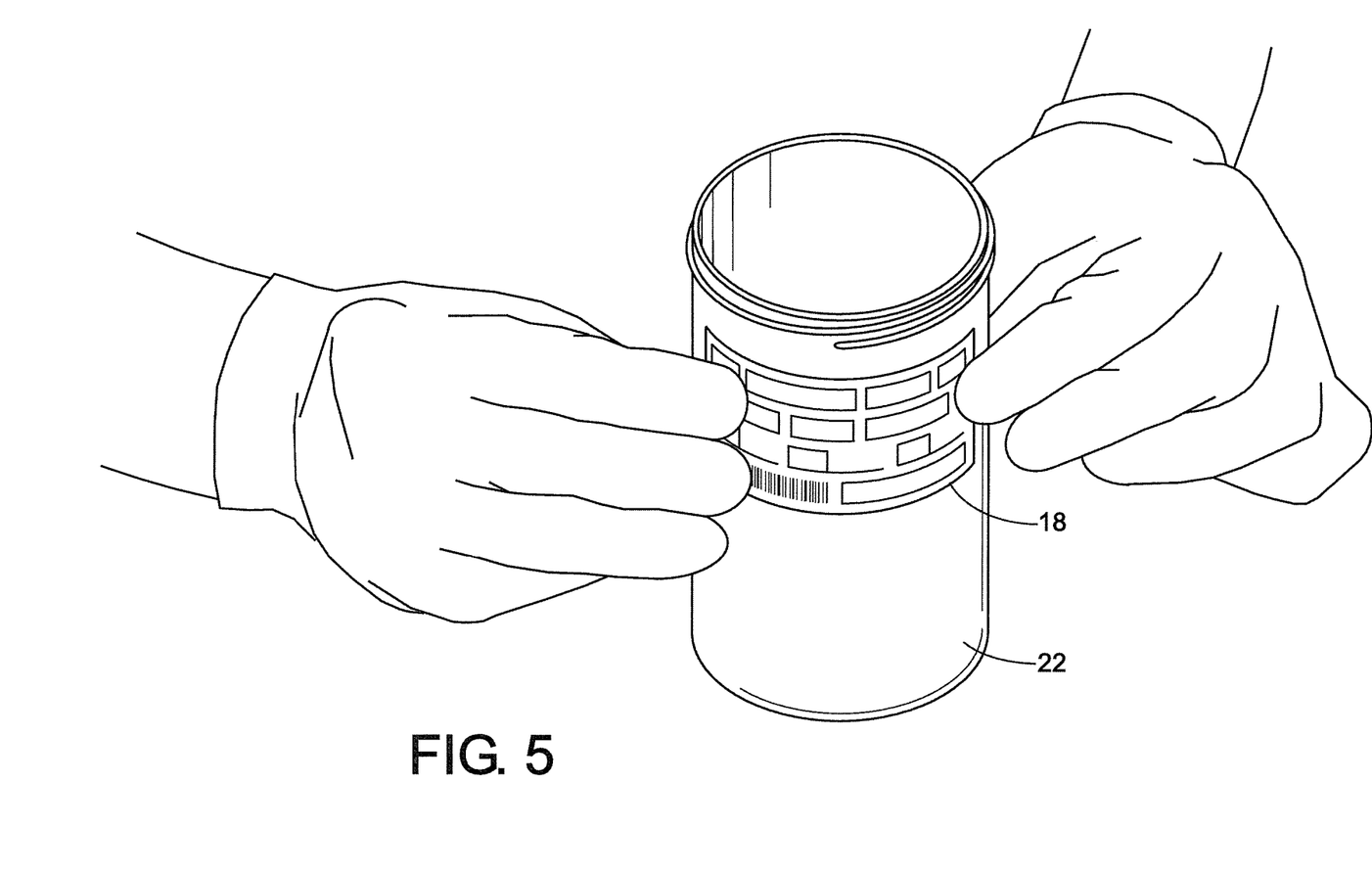
FIG. 5 illustrates one embodiment of the labels being applied according to one of the steps in the method.

Referring now to FIG. 5, which illustrates another step in the method according the present disclosure. This figure illustrates a user applying the label 18 to an associated medical accessory 22. In this embodiment that accessory is a cup 22. However, the associated accessory may be a variety of different objects, including a medical syringe, a tub, a basin, a towel, etc.

The medical accessory into or onto which a medication will be dispensed may be sterile. In order to maintain sterility the user (who may not be sterile) may not be able to come in contact with the label 18 or the medical accessory 22. Therefore, the non-sterile user may not be able to apply the label 18. However, that user may touch the outside of one of the first or second flexible plastic sheets 10, 12, to flip the label 18 to the sterile field. In this form, both the inside the outside of the container in the sterile field 22 and the label 18 can remain sterile and be used in a sterile field. Furthermore, the medication dispensed into the new container 22 within the sterile field will be properly labeled with the information contained on the label 18. The label 18 may also have information added to it through use of a sterile writing utensil (not shown). This information may include the amount of medication and time such medication was dispensed to the field.

As shown in FIG. 5, a sterile user may apply the label 18 by attaching the label through aseptic technique. This figure illustrates how a user may apply the label 18 to a different associated medical accessory 22. In this embodiment the accessory is a round cup 22, where the label 18 is intended to wrap around the medical accessory 22.

Figure 6:
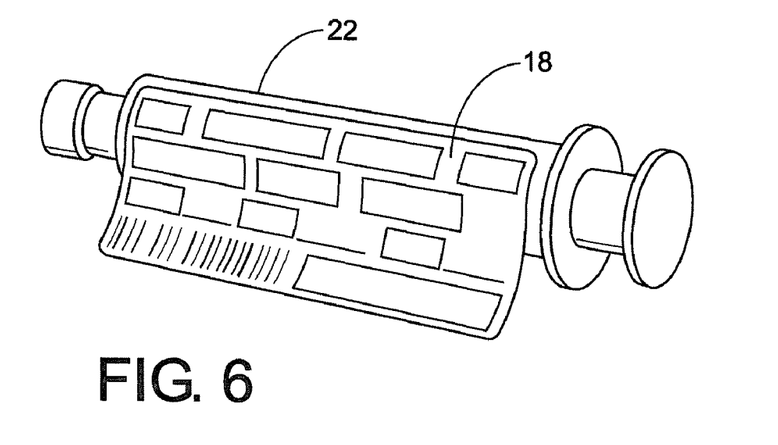
FIG. 6 illustrates another embodiment of the labels according to one of the steps in the method.

As detailed above, and as shown in FIG. 6, the sterile label 18; and the peel pack 8 shown in FIG. 2 may come in different sizes. As shown in FIG. 6, the sterile label 18 may wrap around a syringe 22.

Figure 7A:
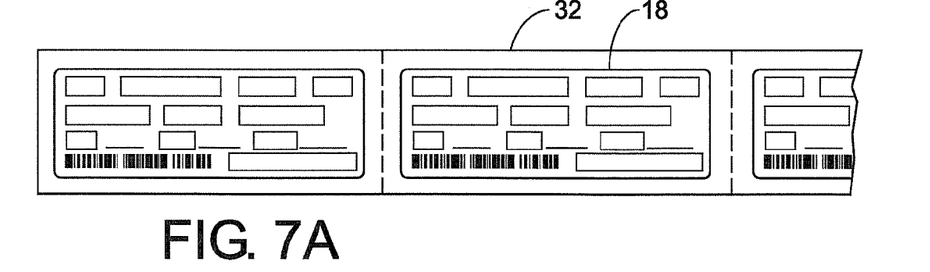
FIG. 7A and FIG. 7B illustrates two embodiments of the labels prepared for printing according to an embodiment of the disclosure.
Figure 7B:
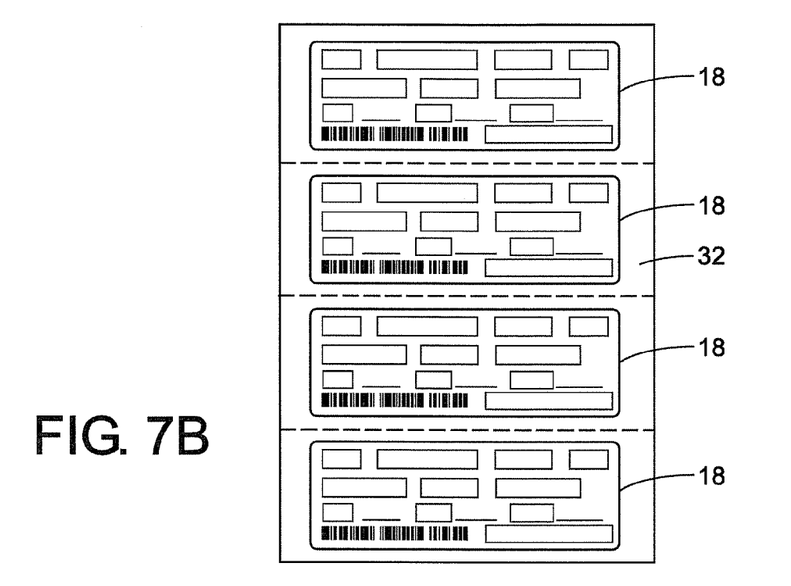

Now referring to FIG. 7A and FIG. 7B which illustrate two embodiments of the labels according to one of the steps in the method. FIGS. 7A and 7B show blank labels that are assembled together for printing. The labels 18 may be joined horizontally and/or vertically for manufacturing purposes. The labels 18 are temporarily affixed to a backing 32 that acts as a carrier for the labels. The labels 18 may be separated from the backing for attachment to a medical accessory. The labels may also be broken up along their perforations in order to be handled individually. Lastly, these labels 18 may be packaged alone or together in groups.

Figure 8:
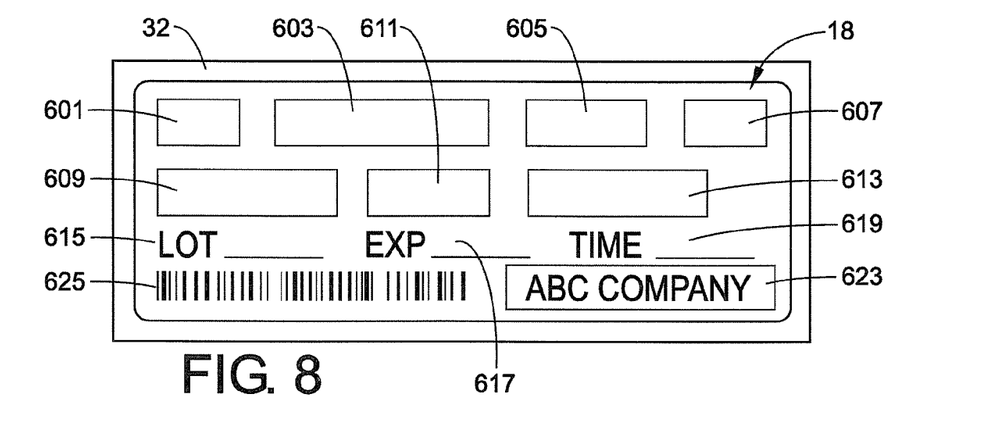
FIG. 8 illustrates one embodiment of a printed label according to this disclosure.

FIG. 8 illustrates one embodiment of a printed label according to this disclosure. It should be noted that this is but one embodiment of a label's formation and this disclosure should not be limited to this one form.

Still referring to FIG. 8, there is a space on label 18, 601, which may be reserved for the strength of the medication. Space 603 may be reserved for the name of the medication and 605 may be reserved for the solute of the medication. Space 607 may be reserved for the route of application of the medication. For example, INJ may stand for injection or TO may stand for topical. Space 609 may be reserved for the concentration of the medication while space 611 may be reserved for a trademark symbol. Space 613 may be reserved for the quantity in the vial while space 615 is reserved for the lot. Space 617 is reserved for the expiration date and 619 for the time. There is also space on label 18 for a bar code 625 and the manufacturer 623.

In this embodiment this label is shown as being 2" long, however, this is but one embodiment. Other embodiments may exist which have some, all, or other information on the label 18. Furthermore, the information directed towards the label 18 may be in different spaces and positioning on the label.

Figure 9:
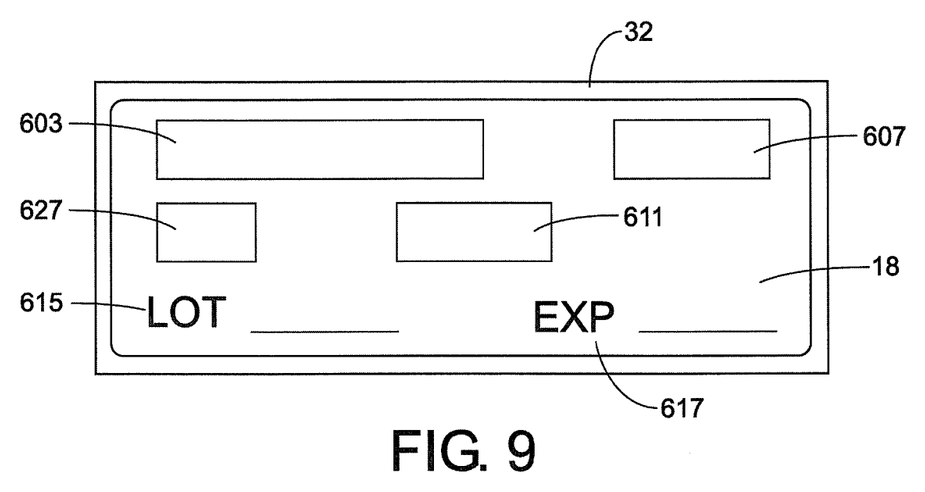
FIG. 9 illustrates another embodiment of a printed label according to this disclosure.

Now referring to FIG. 9 which is another embodiment of the display on the label. FIG. 9 is one embodiment of a non-liquid medical supply. In this embodiment, there is no need for the strength or solvent spaces 601, 605 from FIG. 8 because the medication is not liquid. FIG. 9 also displays a space 603 for the name of the medical supply and space 607 for the route of application. This embodiment also displays space 627 which may be reserved for the size of the medical supply and 611 for the trademark. Space 615 may be reserved for the lot number and space 617 may be reserved for the expiration date of the medical supply.

Figure 10:
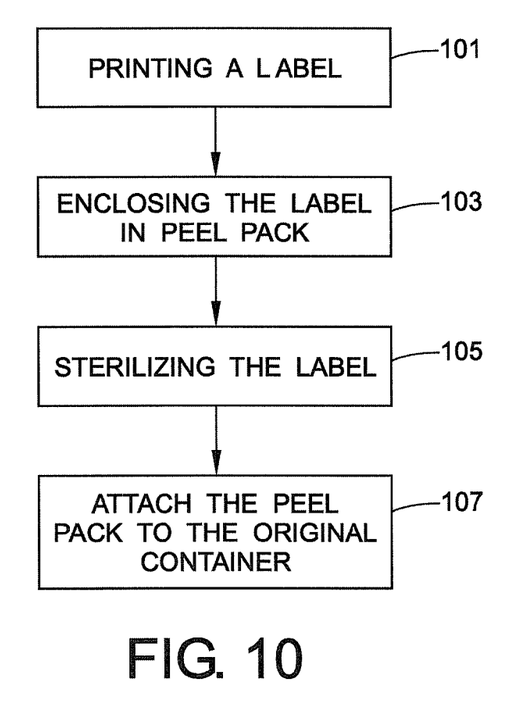
FIG. 10 is a flow chart illustrating the steps of one of the methods according to the present disclosure.

Now referring to FIG. 10 which is a flow chart illustrating the steps of one of the methods according to the present disclosure. The method begins with printing a label 18 having medical information corresponding to a medical product (at step 101). This label 18 may be constructed out of a variety of print media. This print media may also include a variety of useful properties. For example, print media may be synthetic stock, which is waterproof. Print media may also have an adhesive on its second side which may aid in the applying of the label to a medical accessory. Generally, the information corresponding to a medication will be printed onto the label 18. The labels are carried by a backer sheet 32 which consists of a material with a surface from which the labels can readily be peeled. In one embodiment of the disclosure, the label could be subjected to a sterilization process at this time, provided the entire apparatus is assembled in a sterile environment.

The method continues with enclosing the label 18 in a peel pack (at step 103). A peel pack 8 (FIG. 1) will generally consist of at least two sheets of flexible plastic material 10, 12 having adhesive around the edges 14, creating a cavity 20 that may be sterilized. The sheets may also be sealed together through heat sealing or other means. Once the label 18 is in the cavity 20, the label 18 may enter a non-sterile field while maintaining its sterility. This is at least in part because the peel pack will protect the label 18 from its environment. However, the outside of the peel pack may not maintain its sterility.

The method continues with sterilizing the label (at step 105). Generally, a printed label 18 will not be sterilized according to medical sterility standards. Therefore, the next step in the method is to sterilize the label 18 within the cavity 20 so that when the cavity is opened using aseptic technique it may be delivered into a sterile field without compromising the sterility of the field. This is done through a variety of methods which are known in the art. In embodiments where the peel pack includes a sterilization indicator, it will show that the label has been subjected to a sterilization process after this step 105.

The method continues with packaging the sterile label with the corresponding medication (at step 107). The packaging of the sterile label may also be secured to the medication container with a tamperproof seal 34, thereby providing an additional or alternate means of attachment to the container. The seal may also provide a means for the user to identify whether the package has been separated from its corresponding container. This step will help reduce human error by keeping the corresponding medication and the sterile label in relative contact with each other. Furthermore, when the medication is ready to be used, the corresponding label will be near it, ready to be placed on the medical accessory located in the sterile field to be associated with the medication or solution. It should be noted that the medication may also be sterile and similarly be placed inside of a peel pack. When the peel pack is used the medication container and/or label may be placed on or in a medical accessory by a scrubbed medical professional, without compromising the sterility of the sterile field or the sterile label.

Figure 11:
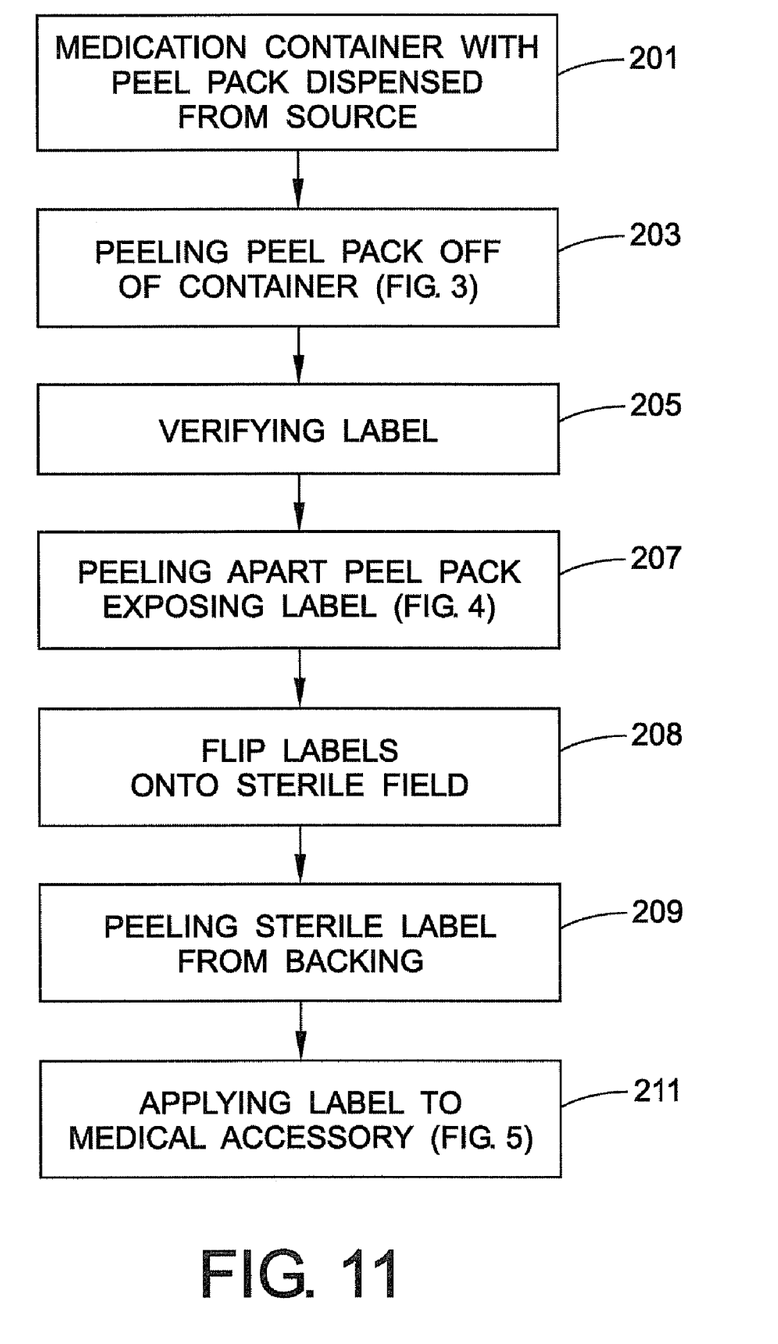
FIG. 11 is another flow chart illustrating the steps of one of the methods according to the present disclosure.

Now referring to FIG. 11, which is a flow chart illustrating steps of another one of the methods according to the present disclosure, e.g. a method of dispensing a medication or supply and its associated labels. The method begins with dispensing the medication with attached apparatus of this disclosure from a source (at step 201). This dispensing source may be a pharmacy which received the medication from a manufacturer from which the medication was shipped. Generally the manufacturer will have printed the labels and sealed the labels inside of the peel pack, sterilized the labels in the peel pack and sterilized the product to which the peel packed labels are attached and sent the ensemble off for shipping to the pharmacy. Generally, a circulating licensed medical professional will receive the medication with the peel pack containing the medication label 18 attached together, from the pharmacy.

The next step according to the method includes peeling the peel pack off of the original medication container (at step 203). This step in the method which is also shown at FIG. 3, includes peeling the entire apparatus (peel pack) 8 including the sterile label 18) off of the original container in which the medication was packed. This may include a large bottle, a box, a flat package, etc. The peel pack is generally affixed to the medical accessory with a type of adhesive that will stick to a variety of different surfaces. This makes the peel pack very versatile and generally useful on all types of medications.

The method continues with verifying the label (at step 205). The circulating and scrubbed medical professionals may then verify the label 18. This may include many different steps. One of these steps may include verifying that the sterilization indicator 17 indicates the peel pack 8 containing the labels has been subjected to a sterilization process. In this form, the sterilization indicator 17 may be a dot, strip, tape, etc. Another step may include verifying the tamper resistant attachment 34 has not been compromised. In this form, the attachment 34 which may be a small circular dot or band placed on the outside of the peel pack, etc. may indicate that the peel pack has been prematurely removed from the original medication container. In this form, one or both of the licensed medical professionals may recognize this inconsistency. One or both of the licensed medical professionals may also notice that the label 18 may not match what is printed on one of the medications' containers. These steps may also provide a licensed medical professional the ability to determine if the label package and its correspondence to the original medication container has been compromised. Corrective steps, such as discarding the compromised material and obtaining appropriate replacements may be performed.

The method continues with peeling apart the peel pack, exposing the sterile label (at step 207). This step may include the circulating licensed medical professional separating the first and second plastic coverings that form a peel pack to expose the sterile label 18. This will enable a scrubbed medical professional to retrieve the label without compromising the label's sterility.

The method continues with flipping the label into the sterile field (at step 208). If the scrubbed professional is occupied, this step may include the circulating professional using the plastic covering to deliver (or flip) the labels 18 to an appropriate surface in the sterile field without touching the labels or the sterile filed. Sterility is maintained.

The method continues with peeling the sterile label from the backing sheet (at step 209) by the scrubbed professional. Generally, the sterile label 18 will come attached to a backing sheet 32. Once the label is peeled from the backing sheet, the method may conclude with applying the label to a medical accessory (at step 211). The label 18 will generally have an adhesive which will stick the label to a medical accessory. In this form, the label will enable the medical accessory to carry a label that identifies the particular medication that is contained therein or thereon. This process will fall under the guidelines of the various government agencies and other accrediting bodies that regulate this procedure. This method also reduces the chance that a medical accessory will be labeled prior to delivery of a particular medication to the sterile field.

The above description merely provides a disclosure of particular embodiments of the claimed invention and is not intended for the purposes of limiting the same thereto. As such, this disclosure is not limited to only the above described embodiments, rather it is recognized that one skilled in the art could conceive alternative embodiments that fall within the scope of the invention.

We claim:

1. An apparatus for sterile labeling on medications and medical solutions comprising:
   a medication or medical solution in a first container having a sterile interior and a non-sterile exterior;
   at least one sterile printed label containing information specific to the medication or medical solution in a second container having a sterile interior and a non-sterile exterior, the second container comprising a first sheet with a peripheral edge and a second sheet with a peripheral edge, said first sheet peripheral edge being releasably bonded to said second peripheral edge;
   the second container being affixed to the exterior of the first container, whereby the medication or medical solution in the first container may be dispensed into a sterile container in the sterile field and one of the at least one sterile printed labels from the second container may be applied to the sterile container in the sterile field.

2. The apparatus according to claim 1 wherein said first and second sheet are transparent.

3. The apparatus according to claim 1, wherein said sterile labels use indelible ink.

4. The apparatus according to claim 1, wherein said sterile label is produced at a time of bottling the medication or medical solution.

5. The apparatus according to claim 1, wherein said sterile label includes a barcode specific to medication or medical solution.

6. The apparatus according to claim 5, wherein the barcode includes expiration information.

7. The apparatus according to claim 1, wherein said sterile label includes space for additional information to be added by a user.

8. The apparatus of claim 1 wherein the at least one sterile label is printed with a name of the medication and strength of the medication.

9. The apparatus of claim 1 wherein the second container is detachably affixed to the exterior of the first container.

10. A method of maintaining association of label information with a medicine or medical solution to be dispensed in a sterile field comprising:
    providing a medication or medical solution in a first container having a sterile interior and a non-sterile exterior, the first container being adapted to dispense a medication or medical solution in a sterile state;
    providing at least one sterile printed label containing information specific to the medication or medical solution in the first container, in a second container having a sterile interior and a non-sterile exterior, the second container being adapted to dispense the at least one sterile printed label in a sterile state;
    fixing the second container to the exterior of the first container forming a product;
    distributing the product to medical professionals for sterile dispensing of the medication or medical solution and sterile label as part of a medical procedure.

11. The method according to claim 10, wherein printing said label includes printing a bar code corresponding to said medical product.

12. The method according to claim 10, wherein printing said label includes printing manufacture information specific to the medication.

13. The method according to claim 10, wherein printing said label includes expiration information.

14. The method of claim 10 wherein said second container comprises a first sheet of flexible material and a second sheet of flexible material releasably bonded to one another to create the second container with a sterile interior, and the dispensing of at least one sterile printed label through at least partially separating the first and second sheets from one another.

15. The method according to claim 14, wherein dispensing said sterile label includes flipping the label onto a sterile surface.

16. The method of claim 10 wherein the second container is detachably fixed to the exterior of the first container.

17. A method of labeling medications and medical solutions in a sterile field comprising:
    providing a medication or medical solution in a first container having a sterile interior and a non-sterile exterior;
    providing at least one sterile printed label containing information specific to the medication or medical solution in the first container, in a second container having a sterile interior and a non-sterile exterior, the second container being releasably affixed to the exterior of the first container,
    dispensing at least some of the medication or medical solution from said first container into at least one sterile container in the sterile field maintaining the sterility of the medication or medical solution;

dispensing at least one of the sterile printed labels from the second container into the sterile field maintaining the sterility of the at least one label; and, applying the at least one sterile printed label to the at least one sterile container in the sterile field, whereby the at least one sterile container is properly labeled with information identifying the medication or medical solution from the first container.

18. The method according to claim 17, wherein said information specific to the medication or medical solution includes the name of the medication, strength and dosage.

19. The method according to claim 17, wherein said information includes a bar code specific to the corresponding medication.

* * * * *